United States Patent [19]
Beckerbauer et al.

[11] Patent Number: 5,294,493
[45] Date of Patent: Mar. 15, 1994

[54] POLYMERIC FILMS FOR SECOND ORDER NONLINEAR OPTICS

[75] Inventors: Richard Beckerbauer; Hui Hsiung; Mureo Kaku; Jose M. Rodriguez Parada, all of Wilmington, Del.; Wilson Tam, Boothwyn, Pa.

[73] Assignee: E. I. Du Pont de Nemours and Company, Wilmington, Del.

[21] Appl. No.: 728,400

[22] Filed: Jul. 11, 1991

Related U.S. Application Data

[63] Continuation-in-part of Ser. No. 623,586, Dec. 7, 1990, abandoned.

[51] Int. Cl.$^5$ ................................................ B32B 9/04
[52] U.S. Cl. ...................... 428/411.1; 428/421; 428/422; 428/515; 428/520; 428/522; 428/913
[58] Field of Search ............... 428/411.1, 421, 913, 428/515, 520, 522, 422

[56] References Cited

U.S. PATENT DOCUMENTS
5,019,451  5/1991  Lando ........................... 428/411.1

FOREIGN PATENT DOCUMENTS
0294061  12/1988  European Pat. Off. .
91/03504  3/1991  PCT Int'l Appl. .

OTHER PUBLICATIONS
B. Tieke, Adv. Mater. 2 222–231, (1990).
Tredgold et al., Electron. Lett. 24 308–309 (1988).
Anderson et al., Synth. Met. 28 D683–688 (1989).
O. A. Aktsipetrov et al., Sov. Phys. JETP 61 524–530 (1985).
Chem. Phys. Lett., vol. 115, No. 14, Oct. 7, 1991 Abstract No. 115: 137184a.

*Primary Examiner*—Paul J. Thibodeau
*Assistant Examiner*—D. S. Nakarani

[57] ABSTRACT

Films of a multiplicity of adjacent polymeric, amphiphilic monolayers, said film having second order optical nonlinearity which increases with the number of active monolayers are provided, as well as novel polymers from which said films are prepared.

10 Claims, 2 Drawing Sheets

X-TYPE

Y-TYPE

Z-TYPE

POLYMERIC FILMS FOR SECOND ORDER NONLINEAR OPTICS

CROSS-REFERENCE TO RELATED APPLICATION

This application is a continuation-in-part of U.S. Ser. No. 07/623,586, filed Dec. 7, 1990 which is now abandoned.

FIELD OF THE INVENTION

The present invention relates to polymeric films for second order nonlinear optics and the polymers from which said films are fabricated.

BACKGROUND OF THE INVENTION

Second-order nonlinear optical phenomena include many important processes that are widely used today. For example, optical second-harmonic generation is used to convert a laser light of a certain frequency to a light of twice the original frequency (i.e., one half the original wavelength). The linear electro-optical effect, another important example, is commonly used to modulate the phase of a light wave with an electric field.

Second-order nonlinear optical processes can only occur within media that do not possess inversion symmetry, i.e., where at least one polar axis whose positive and negative directions are different can be identified. In a molecular medium, the magnitude of a certain second-order optical nonlinearity is determined by both the corresponding molecular nonlinear optical polarizability (also called "hyperpolarizability") and the degree of the polar molecular alignment. Whether a molecular crystal possesses inversion symmetry or not depends critically on details of the molecular structure. A minor modification of the molecular structure can significantly alter the crystal's symmetry, as well as the molecular alignment. It is therefore difficult to simultaneously optimize both the hyperpolarizabilities and the polar alignment of molecules in a crystal. Furthermore, molecular crystals of high optical quality are often difficult to grow. Therefore, alternative routes for preparing molecular media that exhibit useful second-order nonlinear optical properties are highly desirable.

Since the mid-1980's, The Langmuir-Blodgett method has been recognized as a potential route for fabricating organic thin films for second-order nonlinear optics. The Langmuir-Blodgett method, invented during the 1930's, can be used to deposit thin films of certain organic compounds onto various substrates with the film thickness controlled to within a monomolecular layer. Normally, the compounds must be insoluble in water, as well as amphiphilic—containing both a hydrophilic (water-loving) terminal group and a hydrophobic (water-loathing) group at the opposite end. Such a compound can form a monomolecular layer on the water surface with the hydrophilic group anchored to water and the hydrophobic group pointing away from it, thereby leading to a polar alignment of the molecules. Typical examples of such monolayer-forming compounds are the fatty acid series, $CH_3(CH_2)_nCOOH$ ($n \geq 13$), where the carboxylic acid group is hydrophilic and the alkyl chain is hydrophobic. For nonlinear optical applications, an amphiphilic compound must also exhibit a large hyperpolarizability—achievable by the inclusion of a nonlinear optically active group in the molecule. Updated examples of nonlinear optical amphiphiles are given in the review article by B. Tieke, Adv. Mater. 2 222-231, (1990).

The majority of the reported Langmuir-Blodgett materials for second-order nonlinear optics are monomeric compounds. Recently use of multiple monolayers of polymeric and monomeric compounds have been reported. A second harmonic generation active Langmuir-Blodgett film consisting of alternate monolayers of a vinyl-maleic anhydride copolymer and a monomeric merocyanine dye has been reported by R. H. Tredgold et al., Electron. Lett. 24 308-309 (1988). They found a sub-quadratic dependence of the second harmonic generation intensity on film thickness. B. L. Anderson et al., Synth. Met. 28 D683-688 (1989) reported a new Langmuir-Blodgett film structure with each repeating unit consisting of two monolayers of hemicyanine-dye-grafted polyethers and two monolayers of a fatty acid—i.e., an ABCC-structure. The interlacing layers of the monomeric fatty acid were needed to obtain the desirable quadratic dependence of the second harmonic generation signal on the number of the polymeric nonlinear optical monolayers—for up to ten ABCC units. In virtually all known examples of nonlinear optical Langmuir-Blodgett materials, the hydrophobic groups contain straight long chains of hydrocarbons.

For most compounds synthesized to date for fabricating nonlinear optical Langmuir-Blodgett films, there exist several problems that can severely limit their practical uses: (1) the polar molecular alignment tends to degrade with increasing number of monolayers in the Langmuir Blodgett film; (2) the polar alignment induced during the film formation is not stable; (3) the optical quality of the Langmuir-Blodgett film is poor. Optical second harmonic generation is commonly used to characterize second-order nonlinear optical Langmuir-Blodgett films. Ideally, if the degree of the polar molecular alignment is the same within each monolayer, and if the Langmuir-Blodgett thickness is much less than an optical wavelength, the net second harmonic generation intensity from the entire Langmuir-Blodgett film should increase quadratically with the total number of nonlinear optically active layers. [See, for example, O. A. Aktsipetrov et al., Sov. Phys. JETP 61 524-530 (1985)]. However, in most known cases the increase in the second harmonic generation signal with film thickness is less than quadratic, presumably due to deteriorations of the polar alignment both with increasing film thickness and with time.

It is therefore an object of the present invention to provide a nonlinear optically active film in which the nonlinearity increases with the film thickness.

It is a further object of the present invention to provide a nonlinear optically active film comprising monolayers made of entirely polymeric compounds.

It is a further object of the present invention to provide novel polymers useful in fabricating nonlinear optically active films of improved optical quality and stability.

SUMMARY OF THE INVENTION

The present invention provides a film comprising a multiplicity of adjacent polymeric, amphiphilic monolayers, said film having second order optical nonlinearity which increases with the number of said monolayers which are nonlinear optically active. The films can be of the AB-structure of alternating distinct polymeric monolayers, one or both of which contain nonlinear optically active chromophores. The films can also be of the new ABB or $AB_1B_2$ structure wherein every third polymeric monolayer contains second order nonlinearly polarizable chromophores and is distinct from the remaining two polymeric monolayers which are opposite to each other in orientation and have weak or no nonlinear polarizability. For the AB-type of film when the polymeric backbone is hydrophilic, its substituent side groups are terminated by a hydrophobic moiety. Conversely, when the polymeric backbone is hydrophobic, its substituent side groups are terminated by a hydrophilic moiety. For the ABB or $AB_1B_2$-type of film the second order nonlinearly polarizable chromophore of monolayer A is in a substituent group terminating with a moiety having strong affinity for either the polymeric backbone or substituent groups of the B monolayers.

The present invention further comprises novel polymers used in the above-described films, and the corresponding monomers used in the preparation of these polymers. These polymers comprise repeating units of formulae (1), (2), (3) and (7), having the following structures, or copolymers thereof:

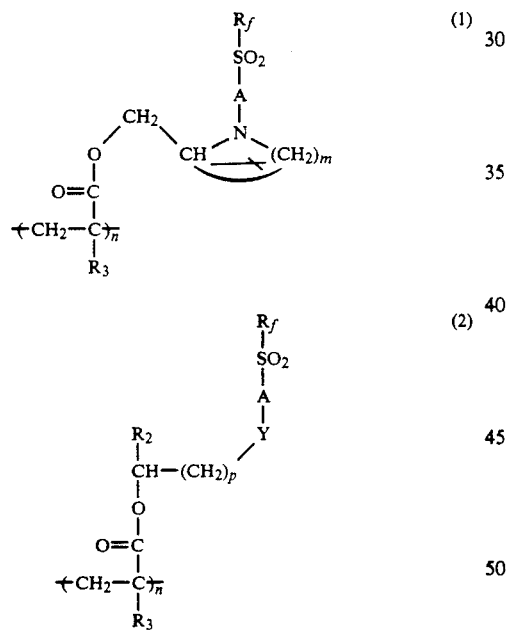

wherein $R_f$ is a linear, branched or cyclic perfluoroalkyl group having at least 4 carbon atoms and having 0 to 3 double bonds;

A for formula (1) and (2) is phenylene or stilbeneyl;

Y is O, S or $NR_1$; provided that when Y is $NR_1$, A for formula (2) is phenylene, biphenylene or stilbeneyl;

$R_1$, $R_2$ and $R_3$ are each independently H or $C_1$ to $C_5$ alkyl;

p is an integer from 0 to 5, provided that p is 1 when Y is $NR_1$ and A is biphenylene;

n is an integer of at least 3; and m is an integer from 2 to 5;

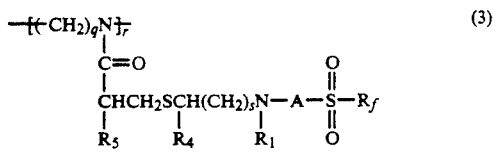

wherein $R_f$ is $(CX_2)_tX$, X is F or H, and t is an integer of from 1 to 18;

$R_1$ is H or an alkyl group of 1 to 5 carbon atoms;

$R_4$ and $R_5$ are each independently a hydrogen or alkyl group of 1 to 17 carbon atoms;

A is phenylene;

q is an integer from 2 to 3;

r is an integer of at least 3;

s is an integer from 0 to 17; and

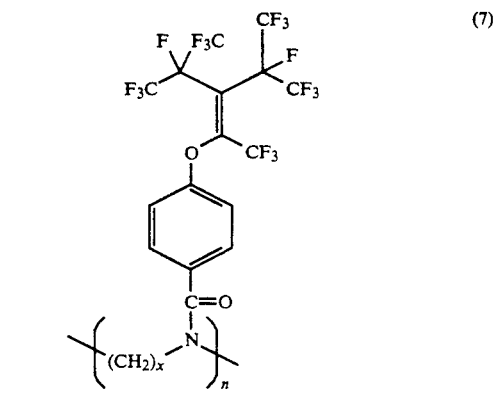

n is an integer of at least 3; and x is an integer from 2 to 3.

DETAILED DESCRIPTION OF THE INVENTION

The present invention comprises films having second order optical nonlinearity made up of a multiplicity of adjacent polymeric amphiphilic monolayers. The monolayers are all polymers, some containing substituent groups having a second order nonlinearly polarizable chromophore, and others containing substituent groups with weak or no hyperpolarizability. The second order optical nonlinearity increases with the number of active monolayers.

The following definitions are used in describing the present invention.

The term "polymer" is used herein to mean macromolecules containing three or more repeating units.

The term "chromophore" is used herein to mean a second order nonlinearly polarizable moiety within a polymer. The chromophore dipoles must be aligned in the same average direction to achieve an increase in second order nonlinear optical activity with an increasing number of monolayers in a film.

The term "polarizable" is used herein to mean the capacity of a material to acquire an induced oscillating dipole moment when an oscillating field such as light passes through the material.

The term "hyperpolarizability" is used herein to mean nonlinearly polarizable. The induced oscillating dipole moment is no longer linearly proportional to the applied oscillating field.

The term "polymer A" is used herein to denote a polymer containing a second order nonlinearly polarizable chromophore.

The term "polymer B" is used herein to denote a polymer having weak or no second order nonlinear optical polarizability compared to a polymer A, or a polymer having second order hyperpolarizability which is opposite in sign relative to a polymer A.

The term "monolayer A" is used herein to mean a monomolecular layer of a polymer containing a second order nonlinearly polarizable chromophore, an active monolayer.

The term "monolayer B" is used herein to mean a monomolecular layer of a polymer having weak or no second order nonlinear optical polarizability, i.e., a buffer monolayer, or of a polymer whose second order hyperpolarizability is opposite in sign relative to a polymer A.

Figure 2A:
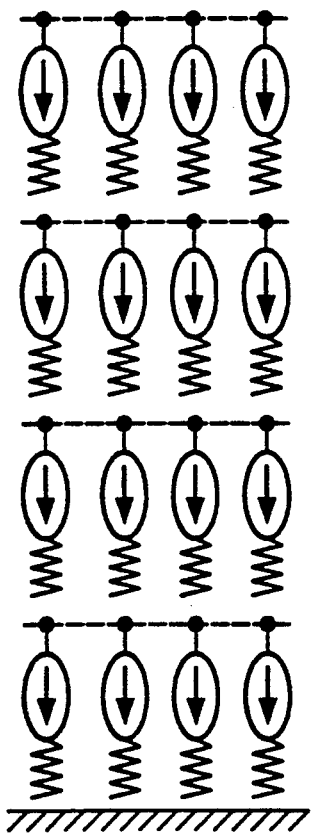
FIG. 2 depicts three types of multilayer Langmuir-Blodgett films. The X-type and Z-type rarely occur because the hydrophilic groups in one monolayer are adjacent to hydrophobic groups in the next monolayer. In the Y-type the molecules in two successive monolayers are oppositely oriented resulting in no net polar alignment.
Figure 2B:
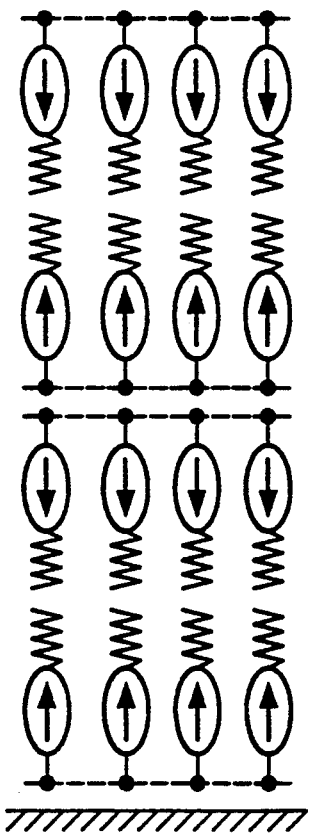
Figure 2C:
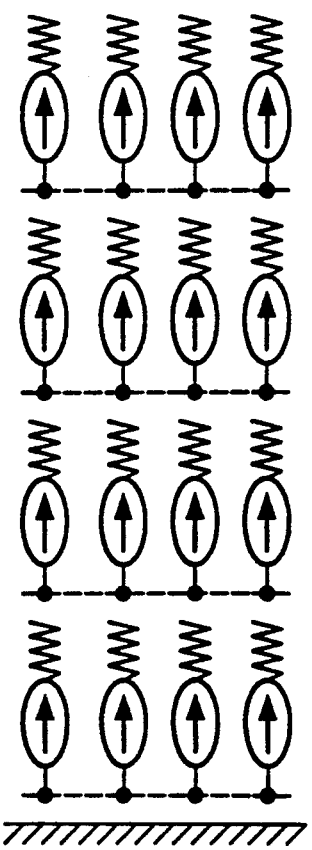
Figure 3A:
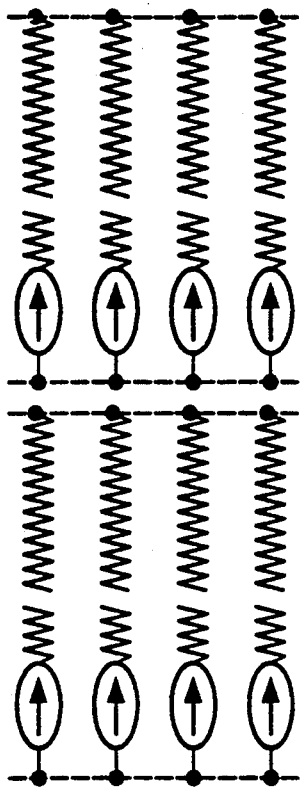
FIG. 3(a) depicts a Y-type Langmuir-Blodgett film of one compound which has second order nonlinear optical activity and a second distinct compound exhibiting little or no optical nonlinearity.
Figure 3B:
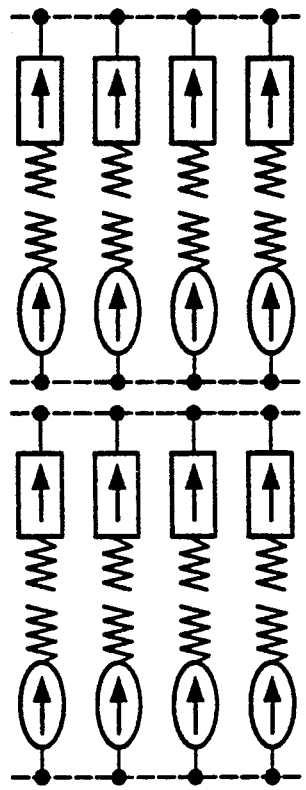
FIG. 3(b) depicts a Y-type Langmuir-Blodgett film of two second order nonlinear optically active compounds with opposite polarities.

Multilayer Langmuir-Blodgett films of a single compound or polymer normally exhibit one of three structures shown in FIG. 2. It is generally accepted that attractive interactions among hydrophilic groups or among hydrophobic groups in neighboring monolayers are responsible for a stable multilayer structure—a reason why the X- and Z-type structures, where hydrophilic groups in one monolayer are adjacent to hydrophobic groups in the next monolayer, are rare occurences. In a normal Y-type film, though the interlayer interactions are favorable, molecules in two successive layers are oppositely oriented, leading to no net polar alignment. Therefore to obtain useful polar alignment for second-order nonlinear optics, it is often necessary to prepare Y-type Langmuir-Blodgett films that consist of alternate monolayers of two compounds (also known as AB-type films). See FIG. 3. The two building blocks for the AB-type films can be one nonlinear optically active compound and one buffer compound that exhibits little or no optical nonlinearity [FIG. 3(a)], or two nonlinear optically active compounds with opposite polarities in their second-order nonlinear optical responses [FIG. 3(b)].

Figure 4:
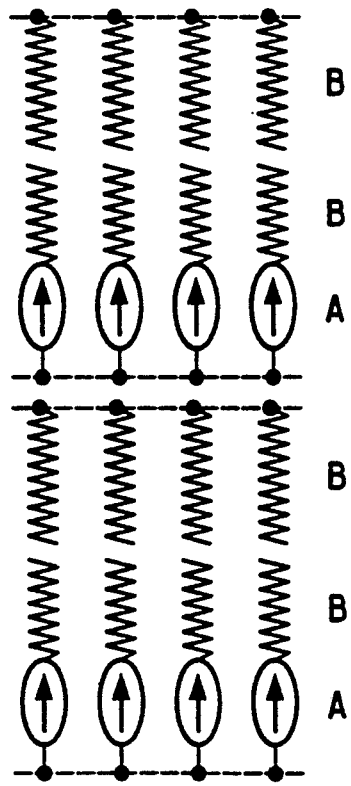
FIG. 4 depicts a Langmuir-Blodgett ABB-type film having one second order nonlinear optically active monolayer and two oppositely oriented buffer monolayers.

The films of the present invention comprise various structural types. These include, for example, previously known structures such as the AB-type. However, the films of the present invention comprise all polymeric monolayers in these known structure types. The films of the present invention also comprise a new structural type denoted as ABB-type, or $AB_1B_2$-type as depicted in FIG. 4.

A film of the AB structure is made up of alternating distinct polymeric, amphiphilic monolayers A and B. A film of the new ABB type is made of repeating units of one polymeric, amphiphilic monolayer A and two monolayers B of a distinct amphiphilic polymer wherein the two B monolayers have opposite dipole orientation to each other. A film of the new $AB_1B_2$ structure is made of repeating units of three distinct polymeric, amphiphilic monolayers A, $B_1$ and $B_2$. The $B_1$ and $B_2$ monolayers have opposite dipole orientation to each other. Other specific structures are included within the present invention, such as one monolayer A combined with more than two monolayers B; or one monolayer A combined with monolayers B of more than two distinct polymers.

For films of the new ABB and $AB_1B_2$ structures the nonlinear optically active monolayers exhibit a net polar alignment, thereby allowing second order nonlinear optic processes. In these structures the second harmonic generation intensity follows quadratic dependence on the number of nonlinear optically active monolayers for at least up to ten ABB or $AB_1B_2$ units (30 monolayers). The second harmonic generation signal from these films exhibits long-term stability measuring in months. For AB-type films prepared from the polymers of the present invention the desirable quadratic dependence of the second harmonic generation intensity is followed on film thicknesses ranging from several to more than 100 monolayers. These films also exhibit long term (months) stability of the second harmonic generation signal.

Figure 1A:
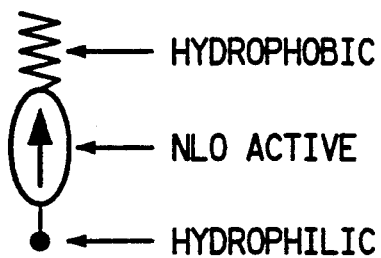
FIG. 1(a) is a schematic of an amphiphilic compound capable of monolayer formation containing a nonlinear optically active group which provides hyperpolarizability to the compound. The arrow indicates the average polar direction of the hyperpolarizability.
Figure 1B:
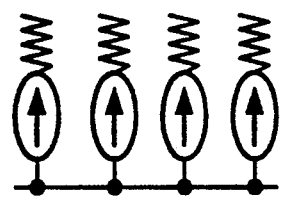
FIG. 1(b) is a schematic of a polymer having a hydrophilic backbone and substituent groups terminated by a hydrophobic group.

The polymers used in the films of the present invention are amphiphilic. See FIG. 1(b). For AB-type films, favorable interactions are required between the polymer A backbone and polymer B backbone and between the polymer A side groups and polymer B side groups for Y-type depositions. For the AB-type films if the polymer backbone is hydrophilic, then the substituent groups of the polymer are terminated by a group which is hydrophobic relative to the backbone. In such polymers where a chromophore group is itself sufficiently hydrophobic, no additional hydrophobic groups are needed. Alternately, if the polymer backbone is hydrophobic, then the substituent groups of the polymer are terminated by a moiety which is hydrophilic relative to the backbone.

It is difficult or impossible to prepare the usual AB-type films from monolayer-forming polymers which are not sufficiently amphiphilic. If the polymer has a hydrophilic backbone, but has nonlinear optically active substituent groups that are not terminated by hydrophobic moieties; or if the polymer has a hydrophobic backbone, but has nonlinear optically active substituents that are not terminated by hydrophilic moieties; it is difficult to prepare AB-type films. For these polymers the new ABB or $AB_1B_2$ deposition sequence can provide additional latitude for the fabrication of multilayer films having second order optical nonlinearity.

For an ABB or AB$_1$B$_2$ structure the second order nonlinearly polarizable chromophore of monolayer A is in a substituent group terminating with a moiety having strong affinity for either the polymeric backbone or substituent groups of monolayer B. For these structures the polymeric backbones of B or B$_1$ and B$_2$ must either be both hydrophobic or both hydrophilic. Thus the interaction between the active and buffer layers will depend in part upon the orientation of each monolayer with respect to the others. Thus, monolayer A itself does not have to be strongly amphiphilic. An example of an ABB film is a monolayer-forming polymer with nonlinearly polarizable active substituent groups which are terminated by a nitro group or cyano group used with a polyoxazoline polymer.

Conventional hydrophobic groups employed in Langmuir-Blodgett materials are straight-chain aliphatic hydrocarbons such as the n-alkyl group. Such saturated hydrocarbons provide little optical nonlinearity, and therefore dilute the net concentration of nonlinear optic chromophores in Langmuir-Blodgett films. Furthermore the hydrocarbon chains are easily deformable and hence considered to be "flexible". In the present invention use of fluorinated hydrocarbon groups is preferred which improve both the optical quality and stability of the films. The advantages of use of fluorinated hydrocarbon groups are twofold. First, fluorocarbons are usually more hydrophobic than hydrocarbons so adequate hydrophobicity can be provided by much shorter fluorocarbon segments than their hydrocarbon counterparts. This effect is used to minimize the dilution of optical nonlinearity. Second, fluorocarbons are more rigid than the corresponding hydrocarbons. The presence of the rigid fluorocarbon groups enhances both the optical quality and stability of the films of the present invention. The tenacity of the films is further improved by use of highly branched hydrophobic groups of fluorocarbons. Any fluorocarbon group can be used herein. Particularly suitable fluorocarbons include linear, branched or cyclic perfluoroalkyl groups having at least 4 carbon atoms and having 0 to 3 double bonds, such as C$_6$ to C$_{12}$ perfluoroalkyleneoxy or C$_6$ to C$_{12}$ perfluoroalkylenethio groups. Other examples include, but are not limited to, CF$_3$(CF$_2$)$_n$— wherein n is greater than or equal to 4, or [(CF$_3$)$_2$CF]$_2$C=C(CF$_3$)O—.

The films of the present invention comprise repeating units of at least one A monolayer combined with at least one B monolayer. The A monolayers comprise an amphiphilic polymer having repeating units of formula (1), (2) or (3) having the following structures, and the B monolayers comprise an amphiphilic polymer having repeating units of formula (4), (5) or (7) having the following structures:

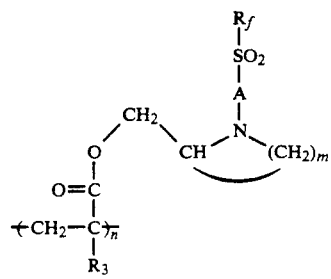
(1)

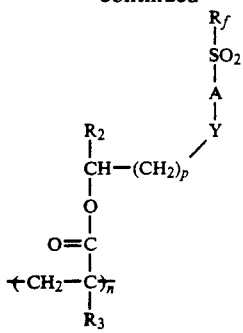
(2)

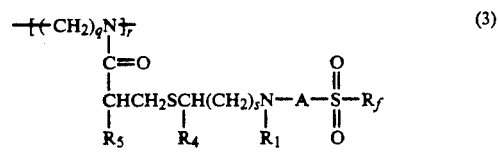
(3)

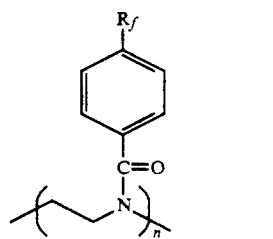
(4)

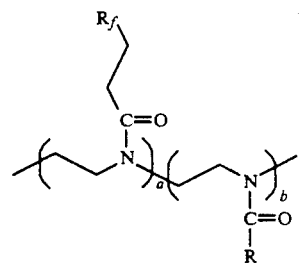
(5)

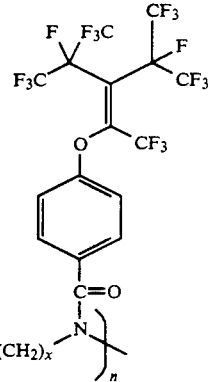
(7)

wherein

R$_f$ for formulae (1), (2), (4) and (5) is a linear, branched or cyclic perfluoroalkyl group having at least 4 carbon atoms and having 0 to 3 double bonds;

R$_f$ for formula (3) is (CX$_2$)$_t$X, X is F or H, and t is an integer of from 1 to 18;

A for formulae (1) and (2) is phenylene or stilbeneyl;

A for formula (3) is phenylene;

Y is O, S, or NR$_1$; provided that when Y is NR$_1$, A for formula (2) is phenylene, stilbeneyl or biphenylene;

R is C$_6$ to C$_{20}$ alkyl;

$R_1$ is H or $C_1$ to $C_5$ alkyl;

$R_2$ and $R_3$ are each independently H or $C_1$ to $C_5$ alkyl;

$R_4$ and $R_5$ are each independently H or $C_1$ to $C_{17}$ alkyl;

m is an integer from 2 to 5;

n is an integer of at least 3;

p is an integer form 0 to 5, provided that p is 1 when Y is $NR_1$ and A is biphenylene;

q is an integer from 2 to 3;

r is an integer of at least 3;

s is an integer from 0 to 17;

x is an integer from 2 to 3; and a and b are each independently an integer of at least 2.

The polymers of formulae (1), (2) and (3) as defined above are the polymer A type containing a chromophore that exhibits large hyperpolarizability. These chromophores may be viewed of comprising three parts, a) an electron accepting perfluoroalkylsulfonyl group, b) an electron donating amino, or ether oxygen or sulfur group, and c) a group bridging the above two which comprises a phenylene, biphenylene, stilbeneyl, or phenylazo-phenylene group. The chromophore is linked to the polymer backbone by a spacer group such as a linear or cyclic hydrocarbon group.

Examples of such polymers include N-substituted polyethyleneimine, polyacrylate, polymethacrylate, or copolymers thereof. These polymers have a hydrophilic backbone relative to fluorocarbon groups and are especially suitable for use with perfluorocarbon hydrophobic groups.

Films of the ABB or $AB_1B_2$ type are prepared from a monolayer of a polymer A having repeating units of formula (6) combined with one or more polymers B having repeating units of formula (4), (5) or (7) having the following structures:

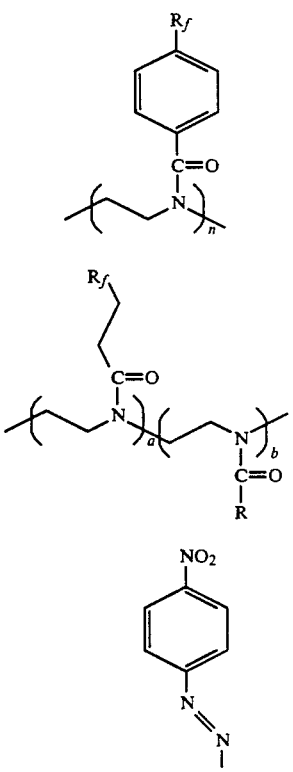

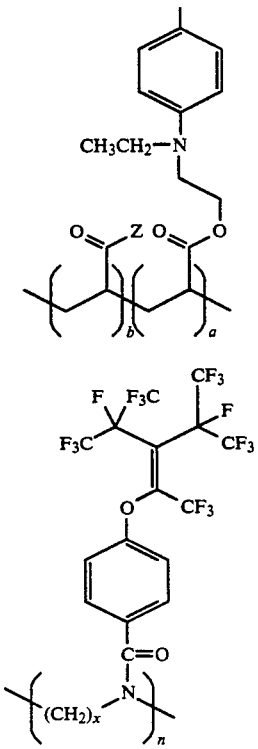

wherein $R_f$ is a linear, branched or cyclic perfluoroalkyl group having at least 4 carbon atoms and having 0 to 3 double bonds;

Z is $OR_6$ or Cl;

$R_6$ is H or $C_1$ to $C_{10}$ alkyl;

n is an integer of at least 3;

a is an integer of at least 2;

b is an integer of at least 2; and x is an integer from 2 to 3;

provided that for formula (6) the ratio of a/b is from about 0.1 to about 1.

Preferred for use herein for the ABB type films are polymers of formulae (6) and (7).

The films of the present invention can be prepared by the Langmuir-Blodgett technique. In the standard Langmuir-Blodgett procedure, a substrate (e.g., glass) slide is repetitively dipped into and withdrawn out of a trough of monolayer-clad water while the surface pressure of the monolayer is kept constant by a compressing barrier at the water surface. During the dipping-withdrawing cycles, the amphiphiles are transferred, monolayer by monolayer, to the surface of the substrate slide. M. Sugi, J. Mol. Electron, Vol. 1, p. 3 (1985), herein incorporated by reference, provides details of the Langmuir-Blodgett technique.

The films of the present invention are useful in second order nonlinear optical processes. The actual efficiency of a particular film in a certain process is determined by a variety of factors, such as the film thickness, the characteristics of light sources, and the geometry of implementation. In particular the films of the present invention are useful in waveguiding devices for efficient nonlinear wavelength conversion.

The present invention further comprises novel polymers useful in the preparation of the above described films and their corresponding monomers. These are represented by the following formulae:

A polymer comprising repeating units of formula (1):

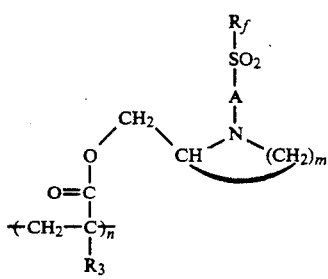

wherein $R_f$ is a linear, branched or cyclic perfluoroalkyl group having at least 4 carbon atoms and having from 0 to 3 double bonds;

A is phenylene or stilbeneyl;

$R_3$ is H or $C_1$ to $C_5$ alkyl;

m is an integer from 2 to 5; and n is at least 3;

A compound comprising the formula (1A):

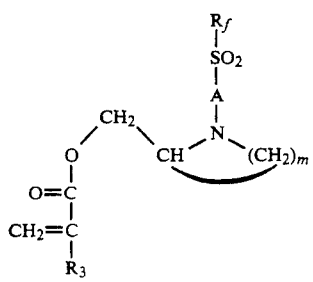

wherein $R_f$ is a linear, branched or cyclic perfluoroalkyl group having at least 4 carbon atoms and having 0 to 3 double bonds;

A is phenylene or stilbeneyl;

$R_3$ is H or $C_1$ to $C_5$ alkyl; and m is an integer from 2 to 5;

A polymer comprising repeating units of formula (2):

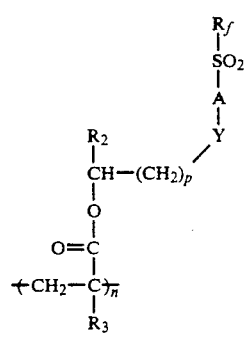

wherein $R_f$ is a linear, branched or cyclic perfluoroalkyl group having at least 4 carbon atoms and having 0 to 3 double bonds;

A is phenylene or stilbeneyl;

Y is O, S or $NR_1$; provided that when Y is $NR_1$, A is phenylene, biphenylene or stilbeneyl;

$R_1$, $R_2$ and $R_3$ are each independently H or $C_1$ to $C_5$ alkyl;

p is an integer from 0 to 5, provided that p is 1 when Y is $NR_1$ and A is biphenylene; and n is an integer of at least 3;

A compound comprising the formula (2A):

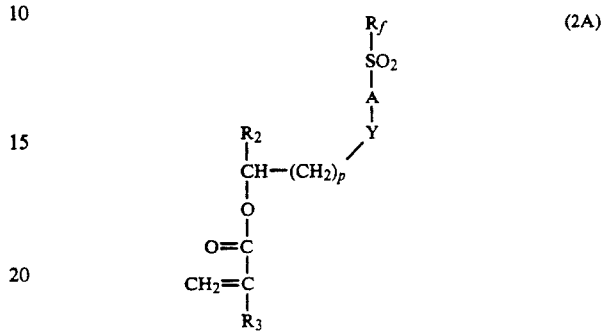

wherein $R_f$ is a linear, branched or cyclic perfluoroalkyl group having at least 4 carbon atoms and having 0 to 3 double bonds;

A is phenylene or stilbeneyl;

Y is O, S or $NR_1$; provided that when Y is $NR_1$, A is phenylene, biphenylene or stilbeneyl;

$R_1$, $R_2$ and $R_3$ are each independently H or $C_1$ to $C_5$ alkyl; and p is an integer from 0 to 5, provided that p is 1 when Y is $NR_1$ and A is biphenylene;

A polymer comprising repeating units of formula (3):

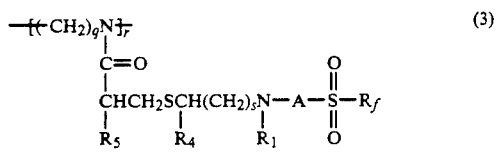

wherein $R_f$ is $(CX_2)_tX$, X is F or H, and t is an integer of from 1 to 18;

$R_1$ is H or an alkyl group of 1 to 5 carbon atoms;

$R_4$ and $R_5$ are each independently a hydrogen or alkyl group of 1 to 17 carbon atoms;

A is phenylene;

q is an integer of 2 to 3;

r is an integer of at least 3; and s is an integer from 0 to 17;

A compound comprising formula (3A) having the following structure:

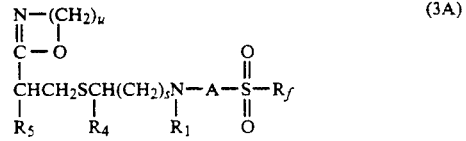

wherein $R_f$ is $(CX_2)_tX$, X is H or F, t is an integer from 1 to 18;

$R_1$ is H or an alkyl group having from 1 to 5 carbon atoms;

$R_4$ and $R_5$ are each independently a hydrogen or alkyl group containing 1 to 17 carbon atoms;

A is phenylene;

u is an integer from 2 to 3; and s is an integer from 0 to 17;

A polymer comprising repeating units of formula (7):

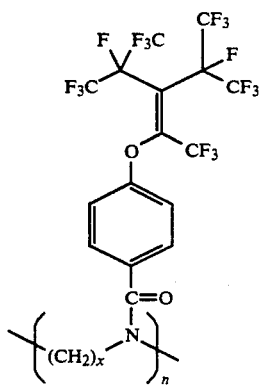

(7)

wherein n is an integer of at least 3; and x is an integer of 2 to 3; and

A compound comprising formula (7A) having the following structure:

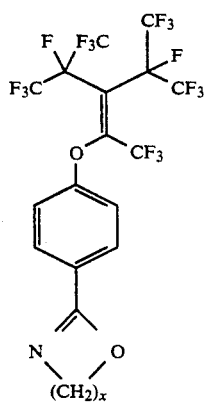

(7A)

wherein x is an integer from 2 to 3.

Compositions of the general formula (1) when A is phenylene are prepared by the reaction of p-perfluoroalkylsulfonylfluorobenzene with cyclic aliphatic compounds containing a ring NH group and a pendent $CH_2OH$ group in polar solvents (e.g., dimethylacetamide, dimethylsulfoxide) in the presence of a base (e.g., triethylamine, potassium carbonate) at temperatures of 25° to 100° C. The products are isolated by precipitation into water and filtration followed by purification by recrystallization (e.g., from ethanol). These products are converted to the acrylate or methacrylate by reaction with the corresponding acid chloride in ether solvents and in the presence of pyridine or triethylamine. The products, isolated after washing of the reaction mixture with aqueous base, are purified by recrystallization or flash column chromatography (alumina or silica gel). These monomers are converted to polymer by reaction in solution (e.g., tetrahydrofuran, chloroform) with typical free radical initiators (peresters, azobisisobuterylnitrile) or by irradiation with ultraviolet light in the presence of a sensitizer (e.g., benzoinmethylether). The polymers are isolated by precipitation into methanol or ether.

Compositions of formula (2) when A is phenylene are prepared in a similar manner except the cyclic amino alcohol is replaced by linear aliphatic amino alcohols of appropriate structure with the proviso that the nitrogen have at least one H substituent.

Compositions of formula (2) when A is biphenylene and Y is $NR_1$ are prepared by the reaction of a 4-amino-4'-perfluoroalkylsulfonylbiphenyl with substituted ethylene oxides followed by the reaction of the formed OH group with acryloyl chloride and polymerization as described above. The biphenyl starting reactants are prepared by the paladium catalyzed coupling of 1-perfluoroalkylsulfonyl-4-trimethylstannylbenzene with p-amino(acetate protected) bromobenzene; the protecting acetate groups are removed after the coupling by hydrolysis under acidic conditions.

Compositions of formulae (1) and (2) when A is stilbenyl are prepared by the reaction of a p-perfluoroalkylsulfonylbenzylbromide with appropriate hydroxyalkylaminobenzaldehydes as described in Organic Reactions, Vol. 14, page 270 (1965)—a general review of the Wittig reaction, which is herein incorporated by reference. Formation of the polymerizable acryloyl derivative and polymerization can be carried out as described above.

Compositions of formula (3) when A is phenyl are prepared by the reaction of a p-perfluoroalkylsulfonylfluorobenzene with thiolalkylamines wherein the amino nitrogen has at least one H substituent followed by the reaction of this product with 2-(2-oxazolyl)-1-alkenes. These products can be polymerized in halocarbon solutions by the addition of, for example, methyl p-toluenesulfonate and heating at 50°-180° C. for 4 or more hours to form the N-substituted ethylenimine polymers.

Compositions of formula (7A) are prepared by reacting 2-(p-hydroxy-phenyl-2-oxazoline) or 2-(p-hydroxyphenyl-2-oxazine) with hexafluoropropene trimer. Compositions of formula (7) are prepared by cationic ring opening polymerization of compounds of formula (7A).

The following examples illustrate the present invention, but are not intended to limit it in anyway.

EXAMPLE 1A

Poly(N-(p-heneicosafluorodecylsulfonylphenyl)-S(+)-2-pyrrolidinylmethyl acrylate)

5 g of N-(p-heneicosafluorodecylsulfonylphenyl)-S(+)-2-pyrrolidinylmethanol, 1 ml of anhydrous triethylamine, 50 ml of methylene chloride and 10 ml of anhydrous tetrahydrofuran (THF) under an argon atmosphere in a flame dried flask equipped with a magnetic stirrer and thermocouple detector was cooled to 0° C. (ice bath). 0.59 ml of freshly distilled acryloyl chloride was added slowly, not allowing the temperature to exceed 4° C. After 1 hour the mixture was warmed to room temperature, the solvent was removed under vacuum. The crude product was chromatographed on activity grade 1, neutral alumina and 2.2 g obtained by elution with methylene chloride was recrystallized from methanol. This product was a single material (gas chromotography) with NMR consistent with N-(p-heneicosafluorodecylsulfonylphenyl) S (+)-2-pyrrolidinylmethyl acrylate. 100 mg of the above product, 4 mg of benzoin methyl ether and 1.6 mg of n-butylmercaptan in 2 ml of THF in a soft glass vial were irradiated with a low pressure, long wavelength ultraviolet lamp (Black Ray Model B-100A) for 1 hour at about 40° C. The mixture was concentrated under nitrogen and then added to methanol to precipitate the product. The solvent layer was decanted and the remaining solid was washed twice with hot methanol. The remaining product (57 mg) had IR and NMR consitent with the above polymer structure. The molecular weight, determined by size exclusion chromatography (THF, 2×100 A and 2×500 A colums-each 300 mm×7.8 mm dia) was 2980 ($M_n$) and was a mixture of material with degrees of polymerization (DP) of 2-16, mainly 4–9. The polymer had a glass temperature (Tg) of 81° C. by differential scanning calorimetry (d.s.c.).

EXAMPLE 1B

Poly(N-p-tridecafluorohexylsulphonylphenyl)-S(+)-2-pyrrolidinylmethyl acrylate

This polymer was prepared as in Example 1A using N-(p-tridecafluorohexylsulfonylphenyl-S(+)-2-pyrrolidinylmethanol as a starting material.

EXAMPLE 2

Poly(N-(p-heneicosafluorodecylsulfonylphenyl)-N-methyl-aminoethyl acrylate)

2.6 g of N-(p-heneicosafluorodecylsulfonylphenyl)-N-methyl-aminoethanol, 0.55 g of anhydrous triethylamine, 40 ml of anhydrous ether and 10 ml of anhydrous THF under an argon atmosphere in a flame dried flask with magnetic stirrer and thermocouple detector were cooled to 0° C. 0.32 ml of freshly distilled acryloyl chloride was added slowly after which time the reaction was kept at 0° C. for 1 hr and then at room temperature for 16 hr. GC analysis showed that a significant amount of starting alcohol was present. An additional 0.32 ml of acryloyl chloride was added and the mixture stirred at room temperature for 1 hr after which time it was extracted with 5% sodium bicarbonate solution and twice with water. The organic layer was separated, dried with magnesium sulfate and then concentrated under vacuum to a tacky, yellow-white solid. This product was recrystallized from ethanol to yield 0.6 g of white solid, a single material by gas chromatography, with NMR consistent with N-(p-heneicosafluorodecylsulfonylphenyl)-N-methyl-aminoethyl acrylate. 100 mg of this material, 1.8 mg of benzoin methyl ether in 0.6 ml of THF in a soft glass vial were irradiated as in Example 1 to yield 34 mg of polymer (insoluble in hot methanol) with $\bar{M}_n$ (SEC)=3060 (approximately a mixture of DP 2-16, mainly 4–9).

EXAMPLE 3

Poly 2-(2-(2-(N-(4-perfluorodecanylsulfonylphenyl))aminoethyl)thioethyl)-2-oxazoline (a) Reaction of 2-aminoethanethiol with 1-perfluorodecanylsulfonyl 4-fluorobenzene 0.276 g (3.58 m mol) of 2-aminoethanethiol was placed in a 50 ml pre-dried three necked flask. 30 ml of THF and 10 ml of tetraglyme were added in the flask via syringe in $N_2$. 0.115 g (4.79 m mol) of NaH was slowly added into the flask and the mixture was kept stirring at room temperature for a hour. After the addition of 1.620 g (2.39 m mol) of 1-perfluorodecanylsulfonyl 4-fluorobenzene, the reaction mixture was heated to 70° C. for 4 hrs. The reaction mixture was then poured into 300 ml of ice-water with vigorous stirring to quench the reaction. The crude compound was collected into a fritted funnel. The obtained compound was dissolved in 200 ml of chloroform and the insoluble portion removed by filtration. The solution was washed by 1% HCl aq, sat NaCl aq, 5% $NaHCO_3$ aq and followed by NaCl aq solution many times. The solvent was removed by evaporation under vacuum. The obtained brown powder was washed with petroleum ether and dried. The yield was 0.910 g (51.8%) of 2-(N-(4-perfluorodecanylsulfonylphenyl))aminoethanethiol.

mp: 97.7° C. (characterized by DSC).

IR(KBr): $\vee$(RR′NH) 1570 $cm^{-1}$, $\vee$(C-F) 1200 $cm^{-1}$, $\vee(SO_2)$ 1140 $cm^{-1}$ $^1$H-NMR (∂ ppm, in $CDCl_3$ with TMS internal standard): 1.44, b, 2 H, NH and SH 3.07, t, 6.0 Hz, 2 H, $NHCH_2CH_2SH$ 3.17, t, 5.9 Hz, 2 H, $NHCH_2CH_2SH$ 7.47, d, 8.8 Hz, 2 H, —$C_6H_2$—NH 7.87, d, 8.8 Hz, 2 H, —$SO_2$—$H_2C_6$—

Elemental Analysis (calculated as $C_{18}H_{10}F_{21}NO_2S_2$); Found: C 29.39%, H 1.68%, N 1.93%; Calcd: C 29.40%, H 1.37%, N 1.90%.

(b) Reaction of 2-(N-(4-perfluorodecanylsulfonylphenyl))aminoethanethiol with 2-vinyl-2-oxazoline 0.20 g (0.28 m mol) of 2-(N-(4-perfluorodecanylsulfonylphenyl))aminoethanethiol and 0.053 g (0.55 m mol) of 2-vinyl-2-oxazoline were added into 10 ml of anhydrous chloroform with stirring at room temperature under nitrogen. After stirring overnight, 100 ml of petroleum ether were added. Then the reaction mixture was cooled to −78° C. to precipitate the target compound. 0.078 g (34%) of 2-(2-(2-(N-(4-perfluorodecanylsulfonylphenyl))aminoethyl)-thioethyl)-2-oxazoline was obtained by filtration. The supernatant was evaporated to give 0.17 g of crude material. The material was recrystallized in chloroform-petroleum ether for polymerization use.

mp: 82.3° C. (characterized by DSC).

IR(KBr): $\vee$(—N=C—O) 1650 $cm^{-1}$, $\vee$(C-F) 1200 $cm^{-1}$, $\vee(SO_2)$ 1140 $cm^{-1}$ $^1$H-NMR (∂ ppm, in $CDCl_3$ with TMS internal standard): 1.73, b, 1 H, NH 2.47, t, 6.6 Hz, 2 H, $SCH_2CH_2$—C(=N)—O) 2.95, t, 6.4 Hz, 2 H, $SCH_2CH_2$—C(=N)—O) 3.00, t, 6.8 Hz, 2 H, $NHCH_2CH_2SH$ 3.20, t, 6.6 Hz, 2 H, $NHCH_2CH_2SH$ 3.82, t, 9.4 Hz, 2 H, $NCH_2CH_2O$ 4.22, t, 9.4 Hz, 2 H, $NCH_2CH_2O$ 7.46, d, 8.8 Hz, 2 H, —$C_6H_2$—NH 7.87, d, 8.8 Hz, 2 H, —$SO_2$—$H_2C_6$—

Elemental Analysis (calculated as $C_{23}H_{17}F_{21}NO_3S_2$); Found: C 32.20%, H 2.14%, N 3.19%; Calcd: C 33.18%, H 2.06%, N 3.36%.

(c) Cationic polymerization of 2-(2-(2-(N-(4-perfluorodecanylsulfonylphenyl)aminoethylthioethyl)-2-oxazoline 0.0306 g (0.0368 m mol) of the compound of Example 3(b) was charged in a 20 ml ampule and the ampule was degassed. After filling it with $N_2$, 0.1557 g of methyl p-toluenesulfonate (MeOTs)/chloroform solution (0.0063 g/0.7355 g) were added into the ampule via syringe under $N_2$. The monomer and initiator ratio was calculated as 5. After sealing the ampule, the polymerization was carried out at 90° C. for 10 days. The reaction mixture was then evaporated and dried at 50° C. in vacuum overnight. The yield was quantitative.

The 1H-NMR spectrum of obtained material showed very broad peaks. But it clearly showed the absence of oxazoline ring's methylene groups. From this evidence, it was concluded that the compound of Example 3(b) was ring-open polymerized to give polymeric material.

EXAMPLE 4

Copolymers of 2-(2-perfluorooctylethyl)-2-oxazoline and 2-decyl-2-oxazoline

All copolymers were obtained by bulk polymerization using 2-(2-perfluorooctylethyl)-2-oxazolinium triflate as initiator. The following example illustrates this procedure:

To a dry 25 mL round bottom flask equipped with magnetic stirring and under Ar atmosphere was added 4.1996 g (8.12 mmol) of 2-(2-perfluorooctylethyl)-2-oxazoline, 0.7355 g (3.5 mmol) of 2-decyl-2-oxazoline and 0.0395 g (0.058 mmol) of initiator. The flask was placed in an oil bath at 130° C. and after ½ hour the reaction mixture was too viscous to stir. The temperature was raised to 150° C. and maintained for 4 hours to finish off polymerization. After this time the flask was cooled to room temperature and the white solid obtained was dissolved in hexafluoroisopropanol and precipitated into methanol. The product was then filtered off and dried under vacuum at 55° C. overnight. 4.67 g of a white fine powder were obtained.

Molecular weights and melting temperature of the materials prepared are shown in Table 1. All copolymers have two melting transitions indicating that these were block copolymers.

TABLE 1

Characterization of 2-Oxazoline Copolymers

| No. | Copolymer[a] (X/Y) | $\overline{M}_n \times 10^{-3}$ [b] | $\overline{M}_w/\overline{M}_n$ | $Tm_1$ (°C.) | $Tm_2$ (°C.) |
|---|---|---|---|---|---|
| 1 | 100/0 | 20.5 | 2.0 | — | 214 |
| 2 | 70/30 | 12.4 | 2.1 | 138 | 210 |
| 3 | 50/50 | 11.4 | 1.5 | 144 | 209 |
| 4 | 50/50 | 28.1 | 1.6 | 148 | 212 |
| 5 | 30/70 | 11.7 | 1.3 | 144 | 203 |
| 6 | 0/100 | 19.1 | 2.5 | 150 | — |

[a]X/Y = Fluorocarbon/Hydrocarbon repeat units
[b]By GPC in HFIP except No. 6 which was measured in THF Monolayers of these polymers were prepared using established procedures as follows. An appropriate amount of dilute solution of polymer (usually 1.0 mg/ml in 10% trifluoroacetic acid in chloroform) was spread on the water surface in a commercial trough (KSV 5000) to form an expanded monolayer. After evaporation of the solvent, the monolayer was compressed by a movable barrier at speeds of 10 to 50 mm/min and the surface pressure was recorded. In this way the pressure-area isotherms for the different polymers were obtained. For deposition of monolayers onto solid substrates, first the monolayer was compressed to the desired surface pressure and then the substrate was dipped and withdrawn at speeds of 2 to 5 mm/min through the monolayer while maintaining the surface pressure constant. With this technique, transfer ratios close to unity were obtained in all cases. All materials formed stable monolayers at the air-water interface with collapse pressures in the range of 55 to 60 mN/m. These monolayers were much more stable than those of the corresponding homopolymers. Uniform Langmuir-Blodgett films were made by either Y or Z deposition of these monolayers onto silicon substrates. Monolayer thickness on these Langmuir-Blodgett films was 17 Å, measured by ellipsometry.

EXAMPLE 5

1 g of 2-[4-(1-oxy-1-trifluoromethyl-2,2-diheptafluoroisopropyl ethylene)-phenyl]-2-oxazoline and 0.0057 g of initiator (N-methyl 2-perfluorooctylethyl-2-oxazolinium triflate) were placed into a 50 ml round bottom flask equipped with magnetic stirring. The flask was evacuated, filled with argon and kept under a slight argon pressure. It was heated to 130° C. in an oil bath and after one hour the polymer became too viscous to stir. The temperature was raised to 150° C. and when the reaction mixture was completely a white solid, it was cooled to room temperature. The polymer was dissolved in hexafluoroisopropanol and precipitated into methanol. The white powder obtained was filtered off and dried under vacuum at 55° C. The yield was 0.87 g. GPC (HFIP, PET std.): $\overline{M}_n = 9560$, $\overline{M}_w = 13100$; DSC: Tg = 120° C.

This polymer formed very stable condensed monolayers at the air-water interface with a collapse pressure of about 50 mN/m and molecular area per repeat at collapse of approximately 43 Å$^2$. The monolayers were transferred onto solid substrates to make multilayer Langmuir-Blodgett films. Monolayer thickness on these films was 13 Å.

EXAMPLE 6

1.5 g of 2-[4-(decafluoro-2H-3-oxahexyloxy)phenyl]-2-oxazoline and 0.0119 g of initiator (N-methyl 2-perfluorooctylethyl-2-oxazolinium triflate) were placed into a 25 ml round bottom flask equipped with magnetic stirring. The flask was evacuated, filled with argon and kept under a slight argon pressure. It was heated to 130° C. in an oil bath and after ½ hour the polymer became too viscous to stir. The temperature was raised to 150° C. and kept there for two hours. The flask was then cooled to room temperature and the polymer was dissolved in CHCl$_3$/TFA and precipitated into methanol. The white powder obtained was filtered off and dried under vacuum at 55° C. The yield was 1.38 g. GPC (HFIP, PET std): $\overline{M}_n = 16000$, $\overline{M}_w = 28100$; DSC: Tm = 245° C.

Stable monolayers were formed at the air-water interface. They collapse at about 57 mN/m pressure and 30 Å$^2$ molecular area per repeat. They were transferred onto silicon substrates to form Langmuir-Blodgett films with thickness of 14 Å per monolayer.

EXAMPLE 7

2.004 g (4.3 mmol) of 2-[4-(n-tridecafluorohexyl)-phenyl]-2-oxazoline and 0.0145 g (0.02 mmol) of initiator (N-methyl 2-perfluorooctylethyl-2-oxazolinium triflate) were placed into a 25 ml round bottom flask equipped with magnetic stirring. The flask was evacuated, filled with argon and kept under a slight argon pressure. It was heated to 100° C. in an oil bath and after 15 minutes the reaction mixture became a waxy solid. After two hours the temperature was raised to 120° C. and kept there for two more hours. The flask was then cooled to room temperature and the polymer was dissolved in hexafluoroisopropanol and precipitated into ethyl ether. The white powder obtained was filtered off and dried under vacuum at 60° C. The yield was 0.75 g. GPC (HFIP, PET std): $\overline{M}_n = 3030$ $\overline{M}_w = 9540$; DSC: Tm = 268° C.

Stable monolayers were formed at the air-water interface. They collapse just below 60 mN/m pressure and 30 Å$^2$ molecular area per repeat. They were transferred onto silicon substrates to form Langmuir-Blodgett films with thickness of 14 Å per monolayer.

EXAMPLE 8

Preparation of Copolymers of Methyl Methacrylate with Acryloyl Chloride and Methacryloyl Chloride Into a set of 30 ml vacuum dried serum bottles were placed 0.05 g Vazo-52 (a,a'-azobis(a,g-dimethylvaleronitrile)) initiator, the appropriate amount of freshly distilled sodium dried THF (tetrahydrofuran) and mixtures of freshly purified monomers as designated in Table 2. The bottles were flushed with dry nitrogen, sealed and placed in an ultrasonic bath at 50° C. for 48 hours. After removal from the bath the samples were retained in the sealed bottles until ready for use. Samples were removed by syringe under positive nitrogen pressure and introduced into nonlinear optically active dye reagent solutions as described hereinafter in Example 10, to form substituted polymers. Bottles were resealed under dry nitrogen, as necessary, to retain an anhydrous inert atmosphere. Acryloyl chloride was purified by distillation, methyl methacrylate by passing through basic alumina.

TABLE 2

| No. | Monomer[a] | mR | Weight (g) | Volume (ml) | moles | THF (ml)[b] |
|---|---|---|---|---|---|---|
| A1 | MMA | 9 | 6.36042 | 6.73774 | $.636042 \times 10^{-1}$ | 21 |
|  | ACl | 1 | .639576 | .574126 | $.706714 \times 10^{-2}$ |  |
| A2 | MMA | 4 | 5.70846 | 6.0471 | $.570846 \times 10^{-1}$ | 21 |
|  | ACl | 1 | 1.29154 | 1.15937 | $.142712 \times 10^{-1}$ |  |
| A3 | MMA | 2 | 4.81928 | 5.10517 | $.481928 \times 10^{-1}$ | 21 |
|  | ACl | 1 | 2.18072 | 1.95756 | $.240964 \times 10^{-1}$ |  |
| A4 | MMA | 1 | 3.67454 | 3.89252 | $.367454 \times 10^{-1}$ | 21 |
|  | ACl | 1 | 3.32546 | 2.98515 | $.367454 \times 10^{-1}$ |  |
| A5 | ACl | 1 | 15 | 13.465 | .165746 | 15 |
| B1 | MMA | 9 | 6.27178 | 6.64383 | $.627178 \times 10^{-1}$ | 21 |
|  | MACl | 1 | .728223 | .680582 | $.696864 \times 10^{-2}$ |  |
| B2 | MMA | 4 | 5.55005 | 5.87929 | $.555005 \times 10^{-1}$ | 21 |
|  | MACl | 1 | 1.44995 | 1.35509 | $.138751 \times 10^{-1}$ |  |
| B3 | MMA | 2 | 4.5977 | 4.87045 | .045977 | 21 |
|  | MACl | 1 | 2.4023 | 2.24514 | $.229885 \times 10^{-1}$ |  |
| B4 | MMA | 1 | 3.42298 | 3.62604 | $.342298 \times 10^{-1}$ | 21 |
|  | MACl | 1 | 3.57702 | 3.34301 | $.342298 \times 10^{-1}$ |  |
| B5 | MACl | 1 | 15 | 14.0187 | .143541 | 15 |

[a]ACl designates acryloyl chloride
MMA designates methyl methacrylate
MACl designates methacryloyl chloride
[b]THF designates tetrahydrofuran

EXAMPLE 9

Preparation of Homopolymers of Acryloyl Chloride and Methacryloyl Chloride

Into 100 ml round bottom flasks containing magnetic stirrers and fitted with reflux condensers, thermometers and nitrogen bubblers were placed 0.05 g Vazo-52 (a,a'-azobis (a,g-dimethylvaleronitrile)) initiator, 25 ml freshly distilled sodium dried tetrahydrofuran and 25 ml of either acryloyl chloride or methacryloyl chloride. The stirred mixtures were then heated to 50° C. for 48 hours using an oil bath for maintaining uniform temperature control. The polymeric product mixtures were then transferred to 60 ml serum bottles, flushed with nitrogen, sealed and stored until ready for use. Samples were removed by syringe under positive nitrogen pressure and introduced into nonlinear optically active dye reagent solutions as described hereinafter in Example 10, to form substituted polymers. Bottles were resealed under nitrogen, as necessary, to retain an anhydrous inert atmosphere.

EXAMPLE 10

Preparation of a Polymer from Polyacryloyl Chloride and N-ethyl-N-(2-hydroxyethyl)-4-(4-nitrophenylazo)benzene [Disperse Red —1]

Into a 500 ml resin kettle reactor fitted with a mechanical blade stirrer, reflux condenser and a nitrogen bubbler to maintain an inlet dry atmosphere over the reaction media, was placed 200 ml freshly distilled sodium dried tetrahydrofuran and 2.5 g (0.00796 moles) purified Disperse Red —1 dye. To this rapidly stirred mixture was added 5.2 ml (0.0318 equivalents) of a 50 Wt. percent solution of polyacryloyl chloride in THF. (This corresponded to a ratio of dye to acid chloride sites of ¼.) The reaction mixture was then heated to 70° C. and stirred for 48 hours under dry nitrogen.

The polymer product was recovered by first adding 100 ml of wet methanol to the warm reaction mixture to encourage conversion of unreacted acid chloride to carboxylic acid followed by precipitation in 700 ml petroleum ether. The product was centrifuged and redissolved THF. The precipitation procedure was repeated using a methanol/pet-ether mixture until thin layer chromatography (TLC) no longer showed evidence of unbound dye. The polymeric product was finally dissolved in THF for storage until ready for use.

Elemental Analysis: % C=52.48, % H=5.30, % N=7.84

Molecular Weight: $\overline{M}_w=6800$, $\overline{M}_n=3650$, P/D=1.87, $DP^a$ 20

Composition by C,H,N=82% acid functionality, 18% Dye attachment.

Molar ratio of dye to acid=¼.8.

EXAMPLE 11

Preparation of a Polymer from Polyacryloyl Chloride and N-ethyl-N-(2-hydroxyethyl)-4-(4-nitrophenylazo)benzene [Disperse Red —1]

Into a 500 ml resin kettle reactor fitted with a mechanical blade stirrer, reflux condenser, addition funnel and a nitrogen bubbler to maintain an inert dry atmosphere over the reaction media, was placed 100 ml freshly distilled sodium dried tetrahydrofuran (THF) and 3.15 g (0.01 moles) purified Disperse Red —1 dye. To this rapidly stirred mixture was added 2.0 ml (0.01 equivalents) of a 50 Wt. percent solution of polyacryloyl chloride in THF. (This corresponds to a ratio of dye to acid chloride sites of 1/1.) After stirring for 20 minutes, 20 ml freshly distilled pyridine was slowly added while heating to 70° C. The reaction was allowed to continue for 24 hours under dry nitrogen and then cooled to room temperature.

The product mixture was divided into 2 equal portions (A and B) and isolated by different isolation and purification procedures. Fraction #1, A, was precipitated by adding to petroleum ether, centrifuged, decanted, redissolved in a mixture of THF and methylene chloride and then reprecipitated from additional petroleum ether. This procedure was repeated until TLC no longer indicated the presence of residual unreacted dye. Fraction #2, B, was stirred into an excess of distilled water to encourage conversion of residual acid chloride to carboxylic acid, and allowed to coagulate. The polymer was removed by centrifugation and redissolved in THF. The product was now reprecipitated in petroleum ether and further purified as described for Fraction #1. The solid polymeric products were finally redissolved in THF for storage until use.

Analysis for Fraction #1

Elemental Analysis: % C=54.10, % H=5.38, % N=8.60

Molecular Weight: $\overline{M}_w$=4330, $\overline{M}_n$=2600, P/D=1.66, $DP^a$ 15

Composition by C,H,N=36% acid functionality, 42% residual acid chloride, and 23% Dye attachment Molar ratio of dye to acid=1.4

Analysis for Fraction #2

Elemental Analysis: % C=57.26, % H=5.63, % N=8.29

Molecular Weight: $\overline{M}_w$=4460, $\overline{M}_n$=2490, P/D=1, $DP^a$ 15

Composition by C,H,N=81% acid functionality, 0% residual acid chloride, and 19% Dye attachment.

Molar ratio of dye to acid=1.4.

EXAMPLE 12 a) Preparation of $Me_3Sn$-phenyl-$SO_2C_{10}F_{21}$ 1.002 g (1.36 mmoles) of Br-phenyl-$SO_2C_{10}F_{21}$ and 50 mg of $Pd(PPh_3)_4$ were stirred for 10 minutes in about 14 ml of dioxane. To this mixture was added 0.888 g (2.71 mmoles) of $Me_3SnSnMe_3$ in 2 ml of dioxane. The mixture was refluxed overnight. Solvent was removed by rotary evaporation and the residue chromatographed over silica gel eluted with 25% $CHCl_3$/hexane to give 0.478 g (0.58 mmoles, 43%) of the desired product as a white solid. Elemental analysis calculated for $C_{19}H_{13}O_2F_{21}SSn$: C: 27.73; H: 1.59; found: C: 27.82; H: 1.57. $^1$H NMR ($CD_2Cl_2$): 8.3 (d, 2H), 8.0 (d, 2H), 0.4 (s with Sn satellite, 9H). $^{19}$F NMR ($CD_2Cl_2$, F11): −126 (s, 2F), −123 (s, 2F), −122 (s, 10F), −120 (s, 2F), −112 (s, 2F), −81 (t, 3F).

b) Preparation of $(CH_3)(CH_3C(O))N$-biphenyl-$SO_2C_{10}F_{21}$ 0.532 g (2.33 mmoles) of $(CH_3)(CH_3C(O))N$-phenyl-Br and 50 mg of $Pd(PPh_3)_4$ were stirred for 10 minutes in about 4 ml of dioxane. To this mixture was added 1.918 g (2.33 mmoles) of $Me_3Sn$-phenyl-$SO_2C_{10}F_{21}$ in 10 ml of dioxane. The mixture was refluxed for two days. Solvent was removed and the residue chromatographed with 25% EtOAc/hexane to give 1.113 g (1.38 mmoles, 59%) of the desired product as a white solid. $^1$H NMR ($CD_2Cl_2$): 8.1 (d, 2H), 7.9 (d, 2H), 7.7 (d, 2H), 7.4 (d, 2H), 3.3 (s, 3H), 1.9 (s, 3H). $^{19}$F NMR ($CD_2Cl_2$, F11): −126.1 (s, 2F), −122.7 (s, 2F), −122 (s, 10F), −120 (s, 2F), −111.8 (s, 2F), −81 (t, 3F).

c) Preparation of $(H)(CH_3)N$-biphenyl-$SO_2C_{10}F_{21}$ 130 mg (0.16 mmoles) of the above product was added 3 ml of EtOH and 3 ml of concentrated HCl. The mixture was refluxed overnight. To the white slurry was added 2N NaOH to pH of 7 and the solid filtered and washed with water. Thus obtained was 123 mg (0.16 mmoles, 100%). $^1$H NMR ($CD_2Cl_2$): 8.04 (d, 2H), 7.8 (d, 2H), 7.5 (d, 2H), 6.7 (d, 2H), 4.1 (s, 1H), 2.9 (s, 3H). $^{19}$F NMR ($CD_2Cl_2$): −112 (s, 2F), −120 (s, 2F), −122 (s, 10F), −122.8 (s, 2F), −126.2 (s, 2F), −81 (t, 3F). Elemental analysis calculated for $C_{23}H_{12}O_2F_{21}SN$: C: 36.09; H: 1.58; found: C: 36.05; H: 1.54.

d) Reaction of the above reagent with Propylene Oxide

To 1.20 g (1.57 mmoles) of the above reagent in a Fischer-Porter vessel was added 10 ml of EtOH and 1.65 ml (23.5 mmoles) of propylene oxide. The vessel was closed and heated for 6 days at 80° C. After cooling to room temperature, the solid was filtered off and washed with a little EtOH and vacuum dried to give 0.715 g (0.87 mmoles, 56%) of the desired product as a light yellow solid. $^1$H NMR ($CD_2Cl_2$): 8.99 (d, J=8.5 Hz, 2H), 7.85 (d, J=8.7 Hz, 2H), 7.61 (d, J=9 Hz, 2H), 6.87 (d, J=9 Hz, 2H), 4.15 (m, 1H), 3.35 (d, J=6.2 Hz, 2H), 3.07 s, 3H), 1.84 (d, J=3.5 Hz, 1H), 1.23 (d, J=6.2 Hz, 3H). $^{19}$F NMR ($CD_2Cl_2$): −120 (s, 2F), −121.8 (s, 10F), −122.7 (s, 2F), −126.3 (s, 2F), −111.8 (S, 2F), −81.0 (t, 3F).

e) Preparation of 4-N-(2-oxyacryloylpropyl)-N-methyl-4'-perfluorodecylsulfonylbiphenyl and polymers therefrom In 3 ml of $CH_2Cl_2$ was added 0.154 g (0.19 mmoles) of the above alcohol from step d). To this mixture was added 30 mg (0.297 mmoles) of $NEt_3$ in 1 ml of $CH_2Cl_2$. The mixture was cooled to −20° C. and 0.02 ml (0.25 mmoles) of acryloyl chloride was added. The mixture was stirred at room temperature for 4 days. Solvent was removed and the residue passed through silica gel eluted with 25% EtOAc/hexane to give 42 mg of the acrylate. This was dissolved in 2 ml of THF and 5 mg of AIBN (2,2'-azobis-[2-methylpropionitrile]) was added. The mixture was refluxed overnight. The solvent was removed and the residue was washed with MeOH and filtered. Thus obtained was 12 mg of the desired polymer.

EXAMPLE 13

A solution of 2(p-hydroxyphenyl)-2-oxazoline (prepared by the method described by D. St. C. Black and M. J. Wade in Aust. J. Chem., 1972, 25, 1797–1810 for 2-(o-hydroxyphenyl)-2-oxazoline) (4.89 g, 0.03 mol) and hexafluoropropene trimer (14.85 g, 0.033 mol) in 80 ml of dimethylformamide and 3 ml trichlorotrifluoroethane was cooled to 15° C. under nitrogen atmosphere. To this solution, 1,4-diazabicyclo[2.2.2]octane (4.04 g, 0.036 mol) in 40 ml dimethylformamide was added dropwise over a ½ hr period. The reaction mixture was allowed to warm up to room temperature during the addition, and it was kept stirring at this temperature for 40 hrs. Then it was poured into 250 ml of ice-water, sodium chloride was added and it was extracted with three 75 ml portions of ethyl ether. The ether extracts were dried over magnesium sulfate and after evaporation of the solvent, a clear oil which solidified upon standing at room temperature was obtained. After two Kugelrohr distillations (120°–128° C. at ~0.1 mmHg) 7.72 g of a white solid with mp 90°–91° C. were obtained. $^1$H NMR ($CDCl_3$), TMS δ ppm): 7.99 (d, 2 aromatic H); 6.95 (d, 2 aromatic H); 4.45 (t, $OCH_2$); 4.07 (t, $NCH_2$). $^{19}$F-NMR ($CDCl_3$), F11, δ ppm): −56.70 (d, 3F); −71.40 (s, 6F); −72.51 (d, 6F); −167.69 (q, 1F); −169.64 (m, 1F).

Elemental Analysis for $C_{18}H_8F_{17}NO_2$:

|  | % C | % H | % N | % F |
|---|---|---|---|---|
| Cal. | 36.44 | 1.36 | 2.36 | 54.44 |
| Found | 36.22 | 1.25 | 2.50 | 54.85 |

EXAMPLES 14–37

Langmuir-Blodgett Film Preparation

A commercial Langmuir-Blodgett-film deposition system (KSV Model 5000) was employed for the fabrication of the alternate-type multilayer films. The system includes two connected troughs (namely, "A" and "B") filled with purified water (distilled and deionized)—each trough for preparing one kind of polymer monolayer. The monolayers were prepared the usual way as follows:

An adequate amount of a dilute solution of a polymer (typically 1.0 mg/ml in $CHCl_3$) was first spread on the water surface to form a low-density monolayer. After the evaporation of the solvent, the monolayer was compressed by a moving barrier to a desirable surface pressure, which was kept constant by the barrier during the entire film deposition process. The substrate glass slides were cleaned in a mixture of $H_2SO_4$ and "Nochromix" (by Godax Laboratories, Inc., 480 Canal Street, New York, N.Y. 10013), followed by a thorough rinse with purified water. The dipping and withdrawing of the glass slide into and out of either trough was controlled in a particular sequence that dictated the multilayer structure of the deposited films. For AB-type films the second order nonlinear optically active Polymer-A monolayer was deposited during the dipping period and the inactive Polymer B monolayer during the withdrawing period. The dipping-withdrawing speed was 5 mm/min., while both polymer monolayers on water were kept at a surface pressure of 35 dyn/cm. For the ABB-type films, the active Polymer-A monolayer was kept at 8 dyn/cm while on water and deposited onto the glass slide during the dipping period, and the inactive Polymer-B monolayer was kept at 35 dyn/cm and an oppositely oriented bilayer was deposited during a complete withdrawing-dipping cycle. Films were prepared as summarized in Tables 3 and 4.

The nonlinear optical characterization of the Langmuir-Blodgett films was performed in an usual way similar to that described in the review article by S. Allen, "Langmuir-Blodgett films for nonlinear optical applications", in *Materials for Nonlinear and Electro-optics* 1989, Inst. Phys. Conf. Ser. No. 103 (Institute of Physics, Bristol and New York, 1989), p. 163, herein incorporated by reference. Here, the Langmuir-Blodgett film was irradiated by a laser beam of wavelength 1047 nm, and the second harmonic light of wavelength 523.5 nm generated by the Langmuir-Blodgett film was detected in the forward direction of the laser beam. Langmuir-Blodgett films containing different numbers of monolayers were prepared and characterized by the second harmonic generation method. The results are summarized in Table 3 (for the AB-type films) and Table 4 (for the ABB-type films). The second harmonic generation data listed in the tables were obtained for the Langmuir-Blodgett films after about a month from their preparation and under the condition that the laser light was p-polarized and was casted onto the Langmuir-Blodgett films with an incident angle of 55 degrees. A slightly wedged Y-cut quartz slab (second harmonic generation susceptibility $\chi^{(2)}_{xxx} = 1.9 \times 10^{-9}$ esu) was used as a reference standard: All the second harmonic generation data of the Langmuir-Blodgett films were determined relative to the maximum second harmonic generation (i.e., the maximum of the so-called Maker fringes) of the quartz slab placed in the position of the Langmuir-Blodgett film and normal to the incident laser beam.

TABLE 3

Examples of the AB-type Films

| Example | Polymer A | Polymer B | No. of Monolayers in LB Films | SHG Intensity Relative to Quartz ($\times 10^4$) |
|---|---|---|---|---|
| 14 | Example 1A | Example 5 | 20 | .25 |
| 15 | Example 1A | Example 5 | 30 | .48 |
| 16 | Example 1A | Example 5 | 40 | .82 |
| 17 | Example 1A | Example 5 | 50 | 1.42 |
| 18 | Example 1A | Example 5 | 60 | 2.14 |
| 19 | Example 1A | Example 5 | 80 | 4.33 |
| 20 | Example 1A | Example 5 | 120 | 6.58 |
| 21 | Example 1A | Example 5 | 160 | 9.20 |
| 22 | Example 1B | Example 5 | 40 | .06 |
| 23 | Example 2 | Example 5 | 20 | .08 |
| 24 | Example 2 | Example 5 | 40 | .27 |
| 25 | Example 2 | Example 5 | 60 | .70 |
| 26 | Example 3C | Example 5 | 40 | .66 |
| 27 | Example 3C | Example 5 | 80 | 2.16 |
| 28 | Example 12E | Example 5 | 20 | .42 |
| 29 | Example 12E | Example 5 | 40 | 2.49 |
| 30 | Example 1A | Example 6 | 20 | .11 |
| 31 | Example 1A | Example 6 | 40 | .35 |
| 32 | Example 1A | Example 7 | 40 | .46 |
| 33 | Example 1A | Example 4 | 40 | .23 |

TABLE 4

Examples of the ABB-type Films

| Example | Polymer A | Polymer B | No. of Monolayers in LB Film | SHG Intensity Relative to Quartz ($\times 10^4$) |
|---|---|---|---|---|
| 34 | Example 11 | Example 5 | 3 | .17 |
| 35 | Example 11 | Example 5 | 6 | .74 |
| 36 | Example 11 | Example 5 | 15 | 3.00 |
| 37 | Example 11 | Example 5 | 30 | 10.83 |

What is claimed is:

1. A film comprising at least ten adjacent monolayers of amphiphilic polymers, said film having second order optical nonlinearity which increases with the number of said monolayers which are nonlinear optically active,
   wherein at least every third monolayer comprises a polymer having substituent groups each containing a second order nonlinearly polarizable chromophore, and each terminated by a hydrophobic moiety comprising a branched or linear fluorocarbon group;
   wherein the remaining monolayers each comprise a polymer having substituent groups with weak or no nonlinear polarizability, and
   wherein one or more of the polymers have a hydrophilic backbone.

2. A film comprising at least ten adjacent monolayers of amphiphilic polymers, said film having second order optical nonlinearity which increases with the number of said monolayers which are nonlinear optically active,
   wherein at least every third monolayer comprises a polymer having substituent groups containing a second order nonlinearly polarizable chromophore;
   wherein the remaining monolayers each comprise a polymer having substituent groups with weak or no nonlinear polarizability terminated by a hydrophobic moiety comprising a branched or linear fluorocarbon group; and
   wherein one or more of the polymers have a hydrophilic backbone.

3. A film comprising at least ten adjacent monolayers of amphiphilic polymers, said film having second order optical nonlinearity which increases with the number of said monolayers which are nonlinear optically active,
wherein at least every second monolayers comprises a polymer A having substituent groups each containing a second order nonlinearly polarizable chromophore and each terminated by a hydrophobic moiety comprising a branched or linear fluorocarbon group;
wherein the remaining monolayers each comprise a polymer having substituent groups 1) with weak or no nonlinear polarizability, or 2) containing a chromophore having second order nonlinear polarizability opposite in sign relative to said chromophore of polymer A; and
wherein one or both of the polymers have a hydrophilic backbone.

4. A film comprising at least ten adjacent monolayers of amphiphilic polymers, said film having second order optical nonlinearity which increases with the number of said monolayers which are nonlinear optically active,
wherein at least every second monolayer comprises a polymer having substituent groups containing a second order nonlinearly polarizable chromophore, and
wherein the remaining monolayers each comprise a polymer having substituent groups with weak or no nonlinear polarizability terminated by a hydrophobic moiety comprising a branched or linear fluorocarbon group, and
wherein one or both of the polymers have a hydrophilic backbone.

5. The film of claims 1, 2, 3, or 4 wherein the hydrophilic backbone comprises a) a N-substituted polyethyleneimine homopolymer of three or more repeating units, b) a polyacrylate homopolymer of three or more repeating units, c) a polymethacrylate homopolymer of three or more repeating units, or d) a copolymer of polyacrylate, polymethacrylate, or N-substituted polyethyleneimine.

6. The film of claims 1, 2, 3, or 4 wherein the fluorocarbon group comprises a $C_6$ to $C_{12}$ perfluoroalkyleneoxy group.

7. The film of claims 1, 2, 3, or 4 wherein the fluorocarbon group comprises $CF_3(CF_2)_n$— wherein n is greater than or equal to 4.

8. The film of claim 1, 2, 3, or 4 wherein the fluorocarbon group comprises branched $[CF_3)_2CF]_2C=C(CF_3)O$—.

9. A film comprising at least ten adjacent monolayers of amphiphilic polymers, said film having second order optical nonlinearity which increases with the number of said monolayers which are nonlinear optically active, wherein the polymeric monolayers comprise repeating groups of two monolayers, each said repeating group comprising one layer A of a polymer having repeating units of formula (1), (2), or (3) combined with one layer B of a polymer having repeating units of formula (4), (5) or (7), wherein formulae (1) through (5) and (7) have the following structures

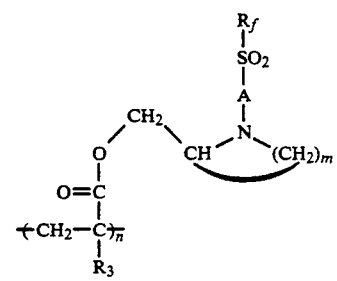

(1)

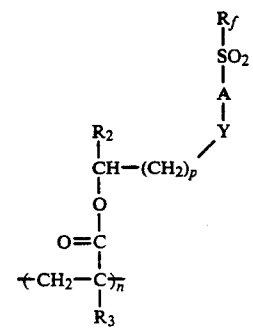

(2)

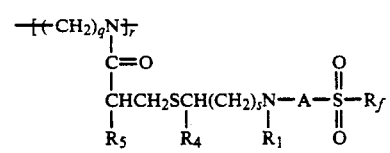

(3)

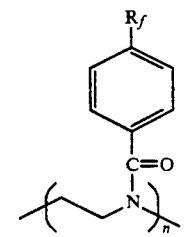

(4)

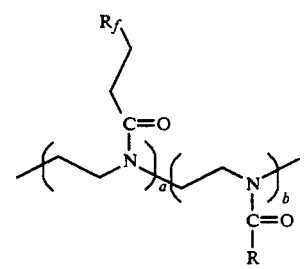

(5)

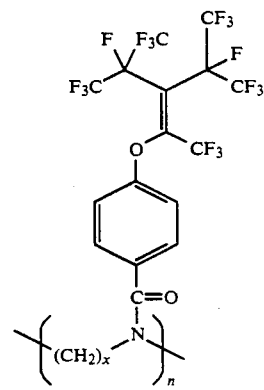

(7)

wherein
- $R_f$ for formulae (1), (2), (4) and (5) is a linear, branched or cyclic perfluoroalkyl group having at least 4 carbon atoms and having 0 to 3 double bonds;
- $R_f$ for formula (3) is $(CX_2)_tX$; X is F or H, and t is an integer of from 1 to 18;
- A for formulae (1) and (2) is phenylene or stilbeneyl; A for formula (3) is phenylene;
- Y is O, S or $NR_1$; provided that when Y is $NR_1$, A for formula (2) is phenylene, stilbeneyl or biphenylene;
- R is $C_6$ to $C_{20}$ alkyl;
- $R_1$ is H or $C_1$ to $C_5$ alkyl;
- $R_2$ and $R_3$ are each independently H or $C_1$ to $C_5$ alkyl;
- $R_4$ and $R_5$ are each independently H or $C_1$ to $C_{17}$ alkyl;
- m is an integer from 2 to 5;
- n is an integer of at least 3;
- p is an integer from 0 to 5, provided that p is 1 when Y is $NR_1$ and A is biphenylene;
- q is an integer from 2 to 3;
- r is an integer of at least 3;
- s is an integer from 0 to 17;
- x is an integer from 2 to 3; and
- a and b are each independently an integer of at least 2.

10. A film comprising at least ten adjacent monolayers of amphiphilic polymers, said film having second order optical nonlinearity which increases with the number of said monolayers which are nonlinear optically active, wherein said monolayers repeat in groups of three as ABB or $AB_1B_2$ in which each repeating unit exhibits a net polar alignment and comprises
  a) one monolayer A of an amphiphilic polymer, and
  b) two monolayers B of a distinct amphiphilic polymer having opposite orientation to each other, or two monolayers $B_1$ and $B_2$ which are distinct from each other as well as distinct from monolayer A and have opposite orientation to each other, wherein monolayer A comprises a polymer having repeating units of formula (6) and each monolayer B, $B_1$ or $B_2$ comprises a polymer having repeating units of formula (4), (5) or (7) wherein formulae (4), (5), (6), and (7) have the following structures

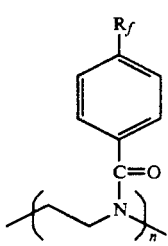
(4)

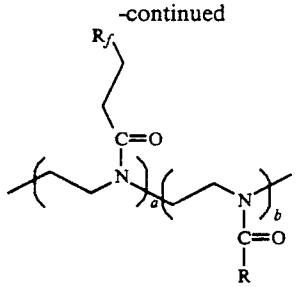
(5)

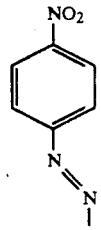
(6)

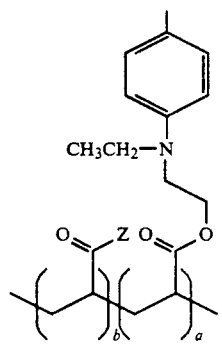

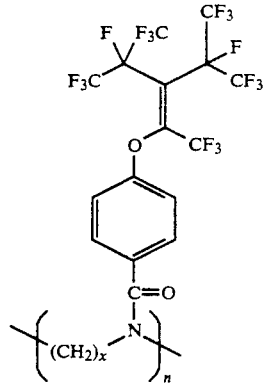
(7)

wherein
$R_f$ is a linear, branched or cyclic perfluoroalkyl group having at least 4 carbon atoms and having 0 to 3 double bonds;
Z is $OR_6$ or Cl;
R is $C_6$ to $C_{20}$ alkyl;
n is an integer of at least 3;
a is an integer of at least 2;
b is an integer of at least 2; and
x is an integer from 2 to 3;
provided that for formula (6) the ratio of a/b is 0.1 to 1.

* * * * *